Figure 1:
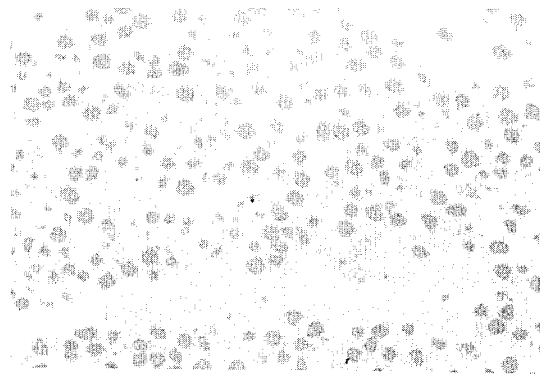

United States Patent [19]

Patroni et al.

[11] Patent Number: 4,797,474
[45] Date of Patent: Jan. 10, 1989

[54] SOLUBILIZATION OF PROTEIN AGGREGATES

[75] Inventors: Joseph J. Patroni, Preston West; Malcolm R. Brandon, Ivanhoe East, both of Australia

[73] Assignee: Bunge (Australia) Pty. Ltd., Australia

[21] Appl. No.: 939,578

[22] Filed: Dec. 9, 1986

[30] Foreign Application Priority Data

Dec. 11, 1985 [AU] Australia .............................. PH 3818

[51] Int. Cl.[4] ................................................ C07K 3/12
[52] U.S. Cl. .................................... 530/351; 530/355; 530/417; 530/418; 530/419; 530/422; 530/423
[58] Field of Search ............... 530/417, 418, 419, 422, 530/423, 351, 355

[56] References Cited

U.S. PATENT DOCUMENTS 4,656,255  4/1987  Seely ................................... 530/418
4,659,568  4/1987  Heilman, Jr. ....................... 530/419

FOREIGN PATENT DOCUMENTS

37973/78  7/1978  Australia ............................. 530/351
2829089  1/1979  Fed. Rep. of Germany ...... 530/418
2397195  9/1979  France ................................ 530/418

Primary Examiner—Ronald W. Griffin
Assistant Examiner—A. Mohamed
Attorney, Agent, or Firm—Merchant, Gould, Smith, Edell, Welter & Schmidt

[57] ABSTRACT

A method for the recovery of proteins which method includes providing a source of protein in an insoluble form, a source of at least one cationic surfactant; treating the insoluble protein with the at least one cationic surfactant in an amount sufficient to effect solubilization without substantial modification to the structural backbone of the protein.

20 Claims, 5 Drawing Sheets

Transmission electron micrograph (x 23,000) of whole cells of E.coli expressing the human malaria parasite antigen fusion protein, Egl3. Inclusion bodies containing the polypeptide are observed as almost transparent globules ranging up to 0.5u in diameter and located within the microorganism.

Fig. 4.

Transmission electron micrograph (x 12880) of whole inclusion bodies containing the infectious bursal disease virus antigen fusion protein. The inclusion bodies are clearly evident as dark rounded particles amidst other cellular debri.

Fig. 5.

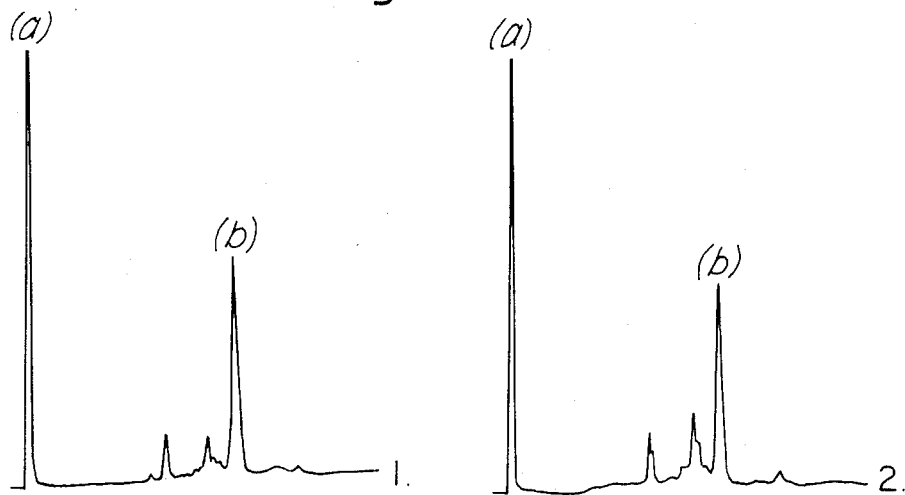

Reversed-phase h.p.l.c. on C1 alkyl bonded silica of two different preparations of inclusion bodies containing recombinent porcine growth hormone in 18% w/v cetyltrimethyl-ammonium bromide 0.05M TRIS pH 10.0 containing 1% B-mercapto-ethanol. Sample (1) contains 39%* and sample (2) contains 27%* porcine growth hormone.
(a)  peak corresponding to the elution of the solvent front
(b)  peak corresponding to the elution of porcine growth hormone as confirmed by coinjection and immunoblot.

*  Percentages refer to the portion of (b) as a percentage of the total area determined from the chromatogram, and are quoted within an estimated experimental area of ± 5%.

Column: TSK-GEL (LC) TMS 250 (5g packing) (Toyo Soda Manufacturing Co. Ltd.)

Fig. 6.

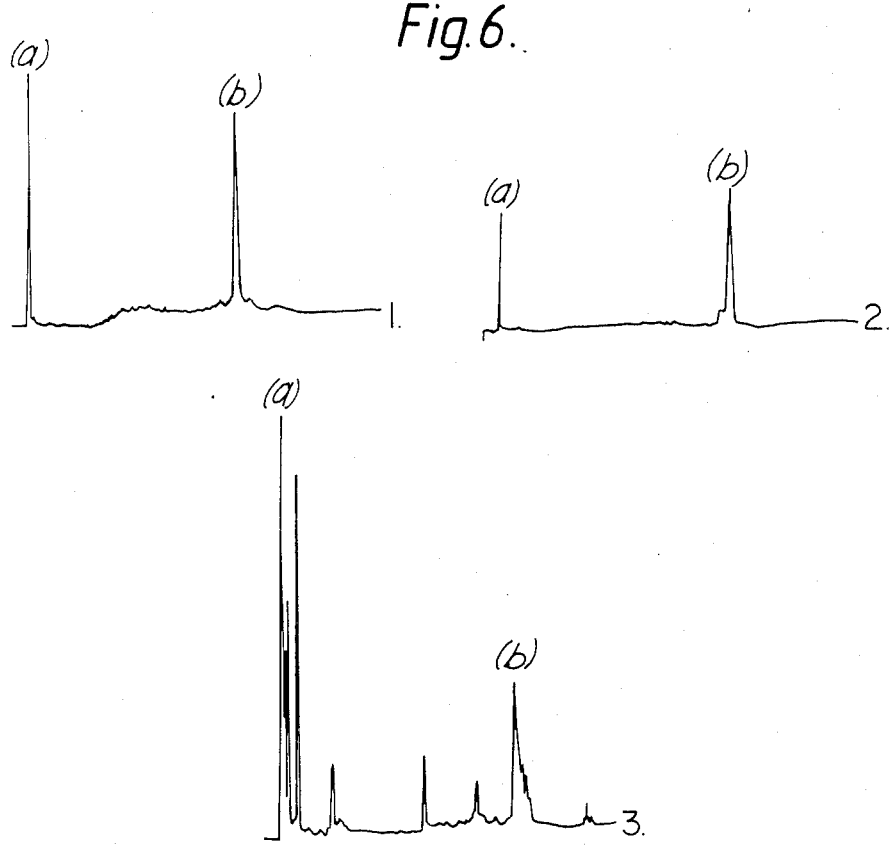

Reversed-phase h.p.l.c. on C3 alkyl bonded silica of (1) 50%* natural porcine growth hormone in 0.05M $NaHCO_3$/0.05M $Na_2CO_3$ pH 10.0. (2) 79%* recombinant porcine growth hormone in 0.05M $NaHCO_3$/0.05M $Na_2CO_3$ pH 10.0 (3) solubilised inclusion bodies containing 20% recombinant porcine growth hormone in 18%* cetyltrimethyl-ammonium bromide 0.05M TRIS pH 10.0 containing 1% dithiothreitol.
(a) peak corresponding to the elution of solvent front
(b) peak corresponding to the elution of porcine growth hormone as confirmed by coinjection and immunoblot analysis; elution time is approximately 21 min.

Column: Ultrapore™ RPSC 5 um (4.6mm x 7.5cm) (Beckman INstruments, Inc.)

SOLUBILIZATION OF PROTEIN AGGREGATES

This invention relates to methods for recovery in soluble form of proteins initially present as insoluble aggregates.

Recombinant DNA technology provides potentially extremely valuable means of synthesizing large amounts of desirable eukaryotic (usually mammalian) proteins such as hormones, interferons, and enzymes. Although it has proved to be relatively easy to manipulate organisms such as bacteria in order to produce the desired protein, the host organism does not normally secrete the protein product into the culture medium. Thus lysis of the organisms (for example bacteria), followed by isolation of the desired protein is usually necessary.

With few exceptions, eukaryotic proteins expressed at high levels in *Escherichia coli* (*E. coli*) are present within the host cell in the form of insoluble protein aggregates (Marston, F. A. O., Lowe, P. A., Doel, M. T., Schoemaker, J. M., White, S., and Angal, S., Bio/Technology, 2 (9), 1984, 729). For example, human insulin produced by *E. coli* is present in the bacterial cells as morphologically characteristic inclusion bodies (Williams, D. C., Van Frank, R. M. Muth, W. L., and Burnett, J. P., Science 215, 1982, 687). These inclusions bodies may occupy a large proportion of the cell volume, and appear to be sites of localised accumulation of the eukaryotic proteins produced by precipitation and aggregation within the cell (ibid).

Whilst the insoluble aggregates can be usefully recovered in high yield by mechanical means, for example, by centrifugation or filtration, it is then usually necessary to render these proteins soluble prior to further purification.

According to the prior art, two principal methods have been used, both of which involve solubilisation with concomitant denaturation of the protein, followed by gradual removal of the denaturant agent; the protein can then slowly renature. In one of these methods solubilsation and denaturation is effected using very high concentrations (6-9M) of compounds such as urea or guanidine hydrochloride in water (International Patent Application WO 83/04418); in the other, the protein is solubilised and reversibly denatured by treatment with alkali at high pH and then returned to a lower non-denaturing pH to allow the protein to renature. The two methods may be combined to give a further improvement in recovery (GB 8407570). However, even with the combined technique the recovery is still only of the order of 30% (GB 8407570).

These methods suffer from serious disadvantages. Those using urea or guanidine hydrochloride utilize reagents which may be very expensive, difficult and hazardous to handle, difficult to remove, ecologically harmful and are required in very large quantities. Solutions of these reagents must either be recycled or disposed of at additional expense. As a consequence these disadvantages tend to detract from their future large scale application (Emtage, J. S., Nature, 317, 1985, 185). Moreover, guanidine hydrochloride may be deleterious to the immunogenicity of the protein.

Alkaline solubilisation using for example sodium or potassium hydroxide is a cheaper alternative, but offers little real advantage in convenience; moreover, at high pH, alkaline aqueous solutions are reactive, causing irreparable damage to the dissolved protein molecule. In both methods, renaturation of the desired protein may be incomplete, resulting in poor recovery, and the processes are slow and tedious.

Accordingly it is an object of the present invention to overcome, or at least alleviate, one or more of the difficulties related to the prior art.

Accordingly, in a first aspect, there is provided a method for the recovery of proteins which method includes providing a source of protein in an insoluble form, a source of at least one cationic surfactant; treating the insoluble protein with the at least one cationic surfactant in an amount sufficient to effect solubilisation without substantial modification to the structural backbone of the protein.

Desirably the amount of the at least one cationic surfactant exceeds the critical micelle concentration.

The present invention is particularly applicable to the solubilization and recovery of biologically active proteins synthesized by microorganisms and eukaryotic cell lines which have been modified by recombinant DNA technology. The protein aggregate may comprise an inclusion body isolated by disruption or lysis of a host cell which may have been transformed or transfected with a vector including a gene coding for the protein. However, it is not restricted thereto. In addition, the present invention is applicable to naturally occurring aggregate protein complexes common to numerous biological systems.

The protein aggregates which may be recovered according to the present invention may be selected from inclusion bodies and cytoplasmic aggregates. The inclusion bodies may be selected from biologically active polypeptides and peptides including growth hormones, interferons, immunogens and lymphokines. As used herein the term "structural backbone" refers to the primary and secondary structure of the protein.

Preferably the at least one cationic surfactant is present in amount of from approximately 2.5 to 50% weight/volume, more specifically 2.5 to 20% weight/volume. The upper limit of surfactant content may vary due to solubility limits of the selected surfactant.

We have now found that it is possible to solubilise aggregates of desired proteins, including inclusion bodies, by treatment of the insoluble form with a cationic surfactant in water, either in the presence or absence of a polar solvent or with the polar solvent alone. The process is rapid (5-60 min), and recovery of the solubilised protein can be optimally effected very easily. Only small quantities of inexpensive reagents, which are readily available and recyclable, are required. For example, the bulk of the solubilising agent may be water.

According to a preferred aspect of the present invention there is provided a method for the recovery of proteins which method includes providing a source of proteins in an insoluble form, a source of at least one cationic surfactant, and a source of at least one polar organic solvent; treating the insoluble protein with a mixture of from approximately 5 to 70% volume/volume of the at least one polar organic solvent and at least one cationic surfactant in an amount sufficient to effect solubilisation without substantial modification to the structural backbone of the protein; and separating the solubilised protein from the resulting solution.

The protein may be maintained in an aqueous solution comprising a polar organic solvent and suitable buffering salts. The presence of a polar organic solvent, such as acetonitrile, preferably at a concentration of 5 to 70% alters the interaction between the insoluble protein and the aqueous solvent, thereby increasing the solubility of the hydrophobic regions of the protein. More preferably the concentration of the organic solvent is 10 to 20%.

Moreover, the incorporation of a cationic surfactant, such as a quaternary ammonium compound, at a level exceeding the critical micelle concentration and sufficient to overcome the associative forces within the aggregate, is highly advantageous and promotes the segregation, disruption and solubilization of the inclusion body constituents.

According to another embodiment of the invention, the addition of an aqueous solution of a suitable surfactant to a dried powder or an aqueous slurry of the protein aggregates is also a highly desirable and efficient means of solubilisation, particularly of whole inclusion bodies. The addition of the at least one cationic surfactant is at levels above the critical micelle concentration and within the limit of its solubility and economy. This procedure is highly desirable for its simplicity; moreover, in contrast to some prior art, the protein may be solubilised in a mild near neutral environment. Due to the nature of the solubilising agent, the recovery method is compatible with later processing steps, in contradistinction to the severe solubilisation treatments of the prior art. The solubilising agent has been found to be compatible with other ingredients utilising the encountered processing of protein aggregates. For example dithiothreitol, mercaptoethanol, reduced glutathione, dimethylsulfone, urea, sodium and potassium hydroxides.

The scope of the invention comprehends the use of all suitable single and multiple chain quaternary nitrogen or phosphorous compounds with various head groups, counter ions and branched or derivatised carbon chains.

Preferably the at least one cationic surfactant is selected from
Cetyl trimethylammonium halide, e.g. bromide,
Cetyl pyridinium halide, e.g. chloride,
Tetradecyl trimethylammonium halide, e.g. bromide,
Dodecyl trimethylammonium halide, e.g. bromide,
Mixed n-alkyl dimethyl benzyl ammonium halide, e.g. chloride (50% C-14, 40% C-12, 10% C-16),
N,N-dimethyl-N-[2-[2-[4-(1,1,3,3,-tetramethyl butyl)-phenoxy]ethoxy]ethyl]benzenemethanaminium halide, e.g. chloride.

It should be understood, however, that the selection of the halide ions is illustrative only. The identity of the anion is unimportant. For example the halide may be substituted by other anions, e.g. sulfonates e.g p-toluene sulfonates.

More preferably the cationic surfactant is cetyl trimethylammonium bromide or cetyl pyridinium chloride.

It is preferred that the cationic surfactant selected is one which does not absorb in the region of the ultraviolet spectrum where polypeptide absorbance is maximal, e.g. cetyl trimethylammonium bromide.

The invention provides significant economic advantages in large scale purification systems. As the cationic surfactants are considered to be active against bacteria, fungi and viruses (Goodman, L. S., and Gilman, S., "The Pharmacological Basis of Therapeutics", 5th Ed., Macmillan Publishing Co. Inc., N.Y., 1975, p 1001), the risk of contamination, sample degradation, and the need for complex and expensive sterile containment facilities are all reduced. Furthermore, only low concentrations of the solubilising agents are required and these may be readily removed from solution by either chromatography, dialysis, Krafft point crystallisation or, additionally, in the case of the organic solvent, by distillation.

The method according to the present invention may include the further step of separating the solubilised protein from the resulting solution.

The separation step may include differential elution of the solubilised protein through a chromatographic column, dialysis, ultrafiltration, differential precipitation, or ligand specific isolation. The chromatographic column may be a high performance liquid chromatography (HPLC) column, optionally a reversed phase high performance liquid chromatography (RP-HPLC) column. A column sold under the trade designation TSK-GEL (LC) and available from Toyo Soda Manufacturing Co. Ltd. (Japan) or Ultrapore RPSC and available from (Beckman Instruments Inc. (Califorina, U.S.A.) have been found to be suitable. Due to the nature of the solubilising agent, the separation step may be conducted utilizing other known forms of chromatography including chromatography of the molecular sieve type, e.g. gel filtration chromatography, anion exchange chromatography, hydrophobic interaction chromatography, and ligand specific chromatography. Preferably the chromatography eluant is an aqueous solution of a cationic surfactant. A dilute solution may be used. The cationic surfactant may be present in amounts of from approximately 0.25% weight/volume to approximately 2.0% weight/volume, more preferably 0.4% weight/volume.

It will be understood that the chromatographic separation also functions to purify the protein product.

It will be understood that the method according to the present invention may be utilised in a method for the analysis of a polypeptide sample wherein the sample to be tested is subjected to the recovery progress thereof. The results may provide a quantitative analysis of the composition of the polypeptide sample.

Embodiments of the present invention will now be illustrated by way of example only with reference to the following non-limiting examples, and the accompanying figures.

In the following examples the transmission electron micrographs were generated as follows:

A small portion of the wet pellet was fixed and embedded into L. R. White resin (London Resin Co., U.K.) and the block sectioned for inspection by electron microscopy using a Philips EM-300 transmission electron microscope.

EXAMPLE 1

Solubilisation of Natural Porcine Growth Hormone

Water-insoluble, lyophilised natural porcine growth hormone isolated in a manner similar to that previously reported[i] (50 mg) was vigorously agitated (30 min, 25°) with an aqueous solution of cetyl trimethylammonium bromide (1.0 ml of 10%) and B-mercaptoethanol (1%). The clarified solution was then centrifuged (13,000 r.p.m., 5 min) on a Beckman Microfuge TM 11 to give a clear supernatant. A 1.0 ml sample of this solution gave a UV absorbance of 72 ($A_{280}\ mm^1\ cm$), indicating that solubilisation had occured.

(i) Reichert, L. E., JR., Methods in Enzymology, XLIII, 1975, 360.

EXAMPLE 2A

Solubilization of Synthetic Porcine Growth Hormone

An experiment was conducted with inclusion bodies obtained from transformed *E. coli* cells. The inclusion bodies, containing 1-190AA methionine-porcine growth hormone, derived from a plasmid, pMG935 were isolated, after cell disruption, by centrifugation. The insoluble protein pellet was washed twice with an aqueous solution of Triton X-100 (0.5%) and EDTA (10 mM) and twice with aqueous EDTA (5 mM); the final pellet was then lyophilised for storage.

The results are illustrated in FIG. 1.

FIG. 1 represents a transmission electron micrograph of methionine-porcine growth hormone inclusion bodies. Clearly visible inclusion bodies of some 0.2 to 0.5 micron in diameter were present along with some fibrous contaminant, most likely cell debris. Magnification is ×6,000.

A portion of the lyophilised inclusion bodies (50 mg) was then treated with aqueous cetyl trimethylammonium bromide (1.0 ml of 10%) in a test tube, and the mixture agitated for 1 hour at room temperature. The mixture was centrifuged (2000 r.p.m., 10 min) on a Beckman Microfuge II to give a clear supernatant and a small insoluble pellet. A small portion of the pellet was fixed and embedded into L. R. White resin and the block section sectioned for comparison by electron microscopy with the untreated material.

Figure 2:
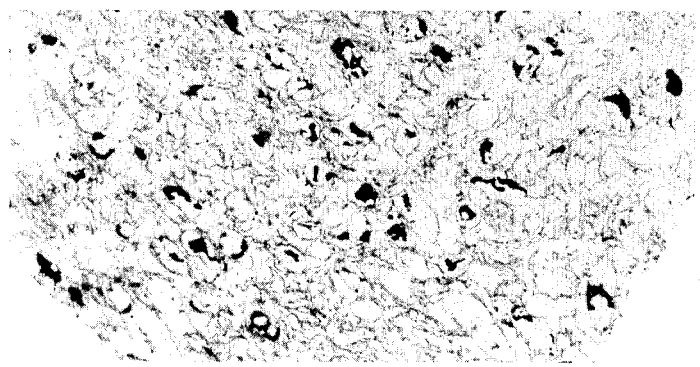

The results are shown in FIG. 2. FIG. 2 represents a transmission electron micrograph of the insoluble residue remaining following solubilization treatment. Magnification is ×4,460. In marked contrast to the untreated material, no inclusion bodies were to be seen after the solubilisation procedure.

EXAMPLE 2B

A similar experiment was conducted to that described in Example 1A above whereby lyophilised inclusion bodies containing the variant 4-190AA porcine growth hormone derived from a plasmid pMG936 (50 mg) were treated with cetyl trimethylammonium bromide (1.0 ml of 107). The mixture was agitated (1 h, room temperature) and centrifuged to give a clear supernatent and a small insoluble pellet. A 1.0 ml sample of the supernatant gave an estimated UV absorbance of 60 ($A_{280\ mm}^{1\ cm}$) indicating that solubilisation had occurred.

EXAMPLE 3

In another experiment, the lyophilised inclusion bodies containing either 1-190AA methionine or the variant 4-190AA porcine growth hormone (50 mg) were treated with a mixture of acetonitrile (0.2 ml), aqueous buffer (0.1M glycine, pH 8.5; 0.8 ml) and aqueous cetyl trimethylammonium bromide (0.5 ml of 10%) in a test tube at 25° C. The mixtures were agitated for 1 hour. Again, as with the previous experiment, substantial solubilization of the inclusion bodies were observed.

EXAMPLE 4

Lyophilised inclusion bodies containing 1-190AA methionine-porcine growth hormone (50 mg) were vigorously agitated with an aqueous solution of one of the cationic surfactants listed below (1.0 ml of 20% in 0.1M TRIZMA, pH 10.0) in a test tube at 25° C. The mixtures were agitated for 30 minutes and then centrifuged on a Beckman Microfuge II for 30 minutes to give clear pale yellow supernatants with negligible pellets in all cases. Again, as with the previous experiments, substantial solubilisation of the inclusion bodies was achieved in each case.

(a) Cetyl pyridinium chloride,
(b) Tetradecyl trimethylammonium bromide,
(c) Dodecyl trimethylammonium bromide,
(d) Mixed n-alkyl dimethyl benzyl ammonium chloride (50% C-14, 40% C-12, 10% C-16),
(e) N,N-dimethyl-N-[2-[2-[4-(1,1,3,3,-tetramethylbutyl)-phenoxy]ethoxy]ethyl]benzenemethanaminium chloride.

EXAMPLE 5

Solubilisation of Human Malaria Parasite

Antigen Fusion Protein

Figure 3:

The B-galactosidase fusion protein (Ag 13) containing a surface antigen from the human malaria parasite *Plasmodium falciparum* was expressed in *E. coli* as unusual almost transparent inclusion bodies (FIG. 3) and was obtained as a gift from Dr. R. F. Anders[ii].

[ii] Coppel, R. L., Cowman, A. F., Anders, R. F., Bianco, A. E., Saint, R. B., Lingelbach, K. R., Kemp, D. J., and Brown, G. V., Nature, 310, 1984, 789.

The wet inclusion body paste (800 mg) containing Ag13, a polypeptide of molecular weight 156kDa, was vigorously agitated with an aqueous solution of cetyl trimethylammonium bromide (1.0 ml of 19% in 50 mM di-sodium ethylenediaminetetraacetic acid (EDTA) and 0.15M tris(hydroxymethyl)aminomethane (TRIZMA), pH 10.0), a cetyl pyridinium bromide (0.25 ml of 10% in 50 mM EDTA and 0.15M TRIZMA, pH10.0) and dithiothreitol (5%) at room temperature.

After some 45 min the initially opaque mixture appeared transparent. The mixture was then centrifuged (13,000 rpm, 10 min.) on a Beckman Microfuge II to give a clear, pale yellow supernatant and a small off-white pellet. The pellet contained no visible remnants of the inclusion bodies upon inspection by electron microscopy.

EXAMPLE 6

Sulubilisation of Infectious Bursal Disease Virus

Antigen Fusion Protein

Inclusion bodies (FIG. 4) containing the Dl fragment of the 32 kDa structural protein from infectious bursal disease virus were obtained as a gift from Dr. K. J. Fahey[iii]. The inclusion bodies were isolated from transformed *E. coli* in a manner similar to that previously described[iv].

[iii] Azad, A. A., Fahey, K. J., Barrett, S. A., Erny, K. M., and Hudson, P. J., Virology, 149, 1986, 190.
[iv] Stanley, K. K., and Luzio, J. P., The EMBO Journal 3, 1984, 1429.

The wet inclusion body paste (100 mg) containing the expressed viral fusion protein was vigorously agitated with an aqueous solution of cetyl trimethylammonium bromide (0.75 ml of 19% in 50 mM EDTA and 0.15M TRIZMA), cetyl pyridinium chloride (0.5 ml of 10% in 50 mM EDTA and 0.15M TRIZMA) and dithiothreitol (5%) at room temperature. After some 30 min the initially opaque mixture appeared completely transparent.

The mixture was then centrifuged (13,000 rpm, 10 min) on a Beckman Microfuge II to give a clear, yellow supernatant and negligible pellet indicating near complete solubilisation. An immuno-dot blot analysis of the supernatant using nitro-cellulose paper and a monoclonal antibody to the Dl polypeptide confirmed the preservation of the active antigenic site on the fused polypeptide.

EXAMPLE 7

Reversed-phase H.P.L.C. on C3 or C1 Alkyl-bonded, Large Pore Silica. The chromatograms illustrated in FIGS. 5 and 6 were obtained by following the protocol outlined below.

Operating parameters are described as follows:

Elution was performed at a flow rate of 0.8 ml/min. at room temperature with water/acetonitrile mixtures containing 0.1% v/v trifluoroacetic acid as modifier: a stepwise linear gradient was constructed from 100% water (0.1 min) to 75% water/acetonitrile over 5 min., to 45% water/acetonitrile over 15 min., to 100% acetonitrile over 5 min. The 100% acetonitrile eluant was maintained for a further 10 min. before re-equilibration prior to the next injection. The composition of the solvent and flow rate may be varied slightly to achieve the desired resolution.

Solutions were all degassed and filtered (0.45 μm); injection volumes of 3 μl were used for the chromatograms displayed in FIGS. 5 and 6. The injection volume can, however, be varied to suit, according to the detection limits and protein concentrations available.

H.P.L.C. was performed on a system comprising two Beckman 114M System Delivery Modules coupled to a 20 μl loop injector and a Beckman 421 Controller. Detection was by UV at 270 nm fixed wavelength on a Beckman 165 Variable Wavelength Detector.

The following words used hereinbefore are registered trade marks: TRITON, L. R. WHITE.

It will be clearly understood that the invention in its general aspects is not limited to the specific details referred to hereinabove.

We claim:

1. A method for the recovery of proteins which method includes providing a source of protein in an insoluble form, a source of at least one cationic surfactant; treating the insoluble protein with the at least one cationic surfactant, in the absence of denaturing guanidine hydrochloride and urea denaturing agents, in an amount sufficient to effect solubilisation without substantial modification to the structural backbone of the protein.

2. A method according to claim 1 wherein the solubilisation is conducted in aqueous solution.

3. A method according to claim 2 wherein the at least one cationic surfactant is present in an amount exceeding the critical micelle concentration.

4. A method according to claim 3 wherein the at least one cationic surfactant is present in an amount of from approximately 2.5% to 50% weight/volume.

5. A method according to claim 4 wherein the cationic surfactant is a quaternary ammonium compound and the insoluble protein is a protein aggregate.

6. A method according to claim 5 wherein the cationic surfactant is selected from surfactants including a cation selected from
Cetyl trimethylammonium cations,
Cetyl pyridinium cations,
Tetradecyl trimethylammonium cations,
Dodecyl trimethylammonium cations,
Mixed n-alkyl dimethyl benzyl ammonium cations,
N,N-dimethyl-N-[2-[2-[4-(1,1,3,3,-tetramethyl butyl)-phenoxy]ethoxy]ethyl]benzenemethanaminium cations.

7. A method according to claim 6 wherein the cationic surfactant is cetyl trimethylammonium bromide.

8. A method for the recovery of proteins which method includes providing a source of proteins in an insoluble form, a source of at least one cationic surfactant, and a source of at least one polar organic solvent; treating the insoluble protein with a mixture of from approximately 5 to 70% volume/volume of the at least one polar organic solvent and at least one cationic surfactant in an amount and sufficient to effect solubilisation without substantial modification to the structural backbone of the protein, in the absence of denaturing guanidine hydrochloride and urea denaturing agents; and separating the solubilised protein from the resulting solution.

9. A method according to claim 8 wherein the at least one cationic surfactant is present in an amount exceeding the critical micelle concentration.

10. A method according to claim 9 wherein the at least one cationic surfactant is present in an amount of from approximately 2.5% to 50% weight/volume.

11. A method according to claim 10 wherein the cationic surfactant is a quaternary ammonium compound and the insoluble protein is a protein aggregate.

12. A method according to claim 11 wherein the cationic surfactant is selected from surfactants including a cation selected from
Cetyl trimethylammonium cations,
Cetyl pyridinium cations,
Tetradecyl trimethylammonium cations,
Dodecyl trimethylammonium cations,
Mixed n-alkyl dimethyl benzyl ammonium cations,
N,N-dimethyl-N-[2-[2-[4-(1,1,3,3,-tetramethyl butyl)-phenoxy]ethoxy]ethyl]benzenemethanaminium cations.

13. A method according to claim 12 wherein the cationic surfactant is cetyl trimethylammonium bromide.

14. A method according to claim 11 wherein the separation step includes differential elution of the solubilised protein through a chromatographic column.

15. A method according to claim 14 wherein the eluant is a dilute aqueous solution of a cationic surfactant.

16. A method according to claim 11 wherein the separation step includes differential precipitation, dialysis, ultrafiltration or ligand specific isolation.

17. A method according to claim 16 wherein the at least one cationic surfactant is cetyl trimethylammonium bromide and the at least one polar organic solvent is acetonitrile.

18. A method according to claim 17 wherein the protein aggregate is an inclusion body isolated by lysis of a host cell.

19. A method according to claim 18 wherein the host cell has been transformed or translated with a vector including a gene coding for the protein.

20. A method according to claim 18 wherein the inclusion body is selected from biologically active polypeptides and peptides including growth hormones, interferons, immunogens and lymphokines.

* * * * *